United States Patent
Friese et al.

(10) Patent No.: US 6,223,583 B1
(45) Date of Patent: May 1, 2001

(54) SENSOR ELEMENT SEAL FOR A DETECTOR

(75) Inventors: Karl-Hermann Friese, Leonberg; Helmut Weyl, Schwieberdingen, both of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/171,687

(22) PCT Filed: Dec. 24, 1997

(86) PCT No.: PCT/DE97/03010

§ 371 Date: Apr. 19, 1999

§ 102(e) Date: Apr. 19, 1999

(87) PCT Pub. No.: WO98/38504

PCT Pub. Date: Sep. 3, 1998

(30) Foreign Application Priority Data

Feb. 25, 1997 (DE) ............................................. 197 07 459

(51) Int. Cl.[7] .......................... G01N 27/12; G01N 30/02; G01N 27/407; H01L 07/00
(52) U.S. Cl. .......................... 73/23.31; 73/31.05; 338/34; 422/94; 123/672
(58) Field of Search .................................. 73/23.31, 116, 73/31.05, 31.06, 23.32; 422/98, 94; 338/34; 123/672, 434

(56) References Cited

U.S. PATENT DOCUMENTS

| 4,130,797 | * | 12/1978 | Hattori et al. | 324/65 P |
|---|---|---|---|---|
| 4,236,138 | * | 11/1980 | Segawa et al. | 338/34 |
| 4,308,518 | * | 12/1981 | Hattori et al. | 338/34 |
| 4,403,207 | * | 9/1983 | Murphy et al. | 338/34 |
| 4,414,531 | * | 11/1983 | Novak | 338/34 |
| 4,665,740 | * | 5/1987 | Matsumoto et al. | 73/116 |
| 4,883,643 | * | 11/1989 | Nishio et al. | 422/94 |
| 4,958,514 | * | 9/1990 | Takami | 73/25.03 |
| 5,031,445 | * | 7/1991 | Kato et al. | 73/23.31 |
| 5,039,972 | * | 8/1991 | Kato et al. | 338/34 |
| 5,182,136 | * | 1/1993 | Saburi et al. | 427/126.3 |
| 5,329,806 | * | 7/1994 | McClanahan et al. | 73/31.05 |
| 5,467,636 |   | 11/1995 | Thompson et al. | 73/23.31 |
| 5,490,412 | * | 2/1996 | Duce et al. | 73/23.31 |

FOREIGN PATENT DOCUMENTS 44 36 580    4/1996  (DE) .
58-079148    8/1983  (JP) .

* cited by examiner

Primary Examiner—Hezron Williams
Assistant Examiner—David J. Wiggins
(74) Attorney, Agent, or Firm—Kenyon & Kenyon

(57) ABSTRACT

A sensor for determining an oxygen content of an exhaust gas of an internal combustion engine includes a flat-plate sensing element that is inserted in a gas-tight fashion via a hybrid seal in a ceramic shaped element that is arranged in a metal housing. The seal includes a powdered sealing packing, both placed around the sensing element in a recess at one end of the ceramic shaped element and a fusible glass seal located above the powdered sealing packing. The seal achieves gas-tight and gasoline-resistant isolation or immobilization of the sensing element in the ceramic shaped element.

16 Claims, 1 Drawing Sheet

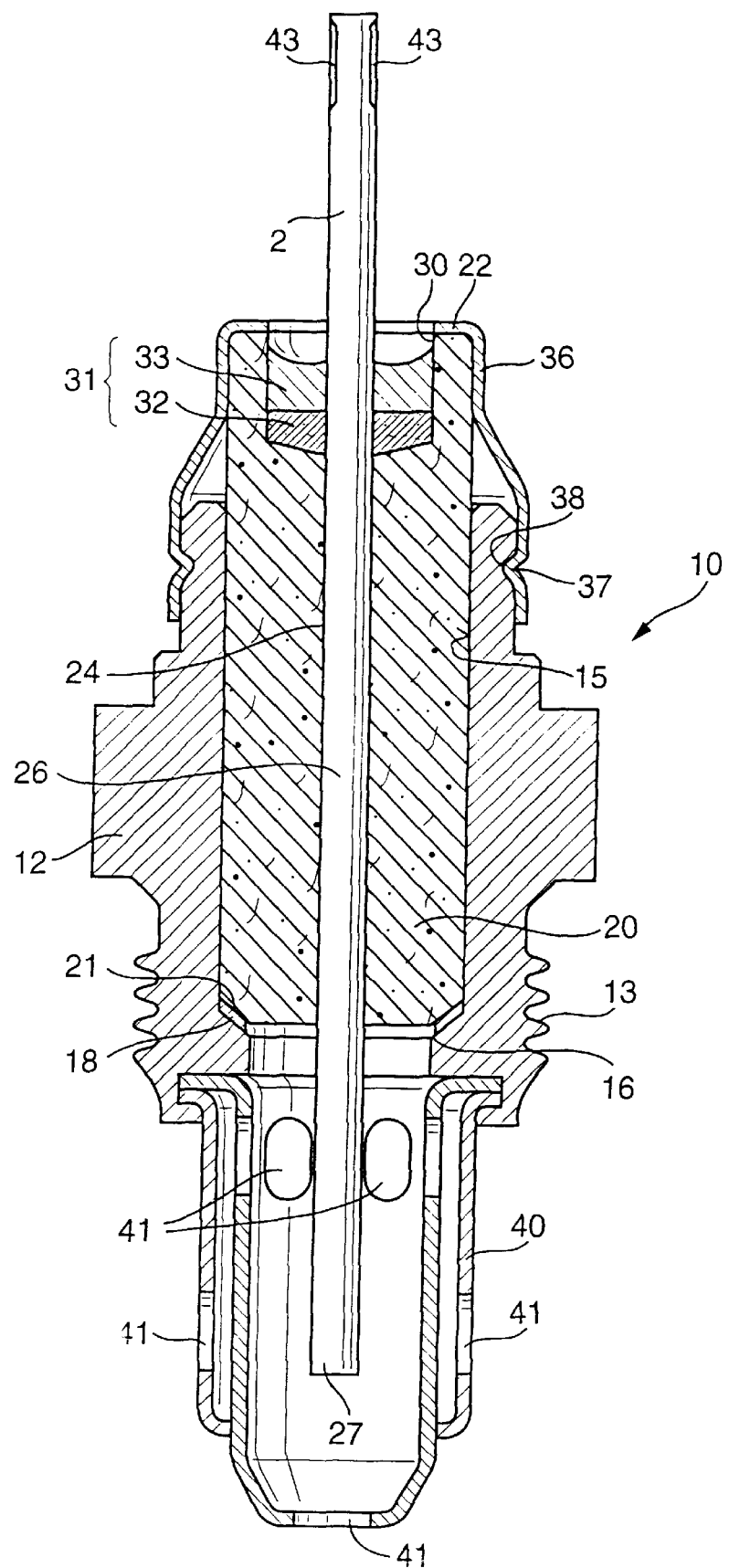

SENSOR ELEMENT SEAL FOR A DETECTOR

BACKGROUND INFORMATION

The present invention relates to a sensor and a seal for a sensing element of the sensor. U.S. Pat. No. 5,467,636 describes a known sensor in which a planar sensing element is immobilized in gas-tight fashion, by way of a sealing element, in a passthrough of a ceramic shaped element. The ceramic shaped element has, on the end surface facing away from the exhaust gas, a recess which surrounds the passthrough and into which a fusible glass seal is introduced. The fusible glass seal surrounds the sensing element in gas-tight fashion at this point, and creates a gas-tight connection to the ceramic shaped element. The fusible glass seal is the only sealing element which implements the seal between sensing element and ceramic shaped element.

SUMMARY OF THE INVENTION

The sensor according to the present invention, has the advantage that by way of the press-in additional seal, pre-immobilization of the sensing element in the ceramic shaped element can be accomplished during manufacture of the fusible glass seal, the pre-immobilization being also maintained during the joining process with the melting of the glass packet associated therewith. The pressed-in additional seal moreover relieves stress on the joining point between the sensing element and the fusible glass seal, both upon cooling after the joining process (because only radial stresses then act on the fusible glass seal), and when the sensor is under thermal and mechanical load, especially under vibratory load. The additional seal moreover prevents the molten glass from penetrating, during the melting process, into the front region of the sensing element which is subject to severe thermal stress when the sensor is used.

It is particularly advantageous to use as the additional seal a powder packing made of graphite or graphite-containing material, since graphite is not wetted or only partially wetted by molten glass. Powder packings made of steatite or similar ceramic materials, which preferably are presintered or pre-compressed so that no disruptive reactions can take place between the powder packing and fusible glass, are economical. A further embodiment of the additional seal consists in the use of ceramic films, for example made of $Al_2O_3$ and/or $ZrO_2$, which are introduced into the recess of the ceramic shaped element and compressed there so as to yield pre-immobilization of the sensing element in the ceramic shaped element. Lithium aluminum silicate glass or lithium barium aluminum silicate glass have proven to be advantageous glasses for the fusible glass seal.

BRIEF DESCRIPTION OF THE DRAWINGS

The FIGURE shows a cross section through a measured-gas-side portion of an electrochemical sensor according to the present invention.

DETAILED DESCRIPTION

An electrochemical sensor for determining the oxygen content in exhaust gases of internal combustion engines has a measured-gas-side section 10 (depicted) and a connector-side section (not depicted) which is sufficiently known. Means for making electrical contact (43) to sensing element 26 are housed in the connector-side section.

The sensor has a metal housing 12 in which a flat-plate sensing element 26, having a measured-gas-side end section 27 and a connector-side end section 28, is arranged. Housing 12 is embodied with threads 13 as mounting means for installation into an exhaust pipe (not depicted). Also configured in housing 12 is a longitudinal bore 15 having a shoulder-like annular surface 16. A metal sealing ring 18, for example, is located on shoulder-like annular surface 16.

A ceramic shaped element 20 having a measured-gas-side end surface 21 and a connector-side end surface 22, and having an axially extending passthrough 24, is inserted into longitudinal bore 15. Ceramic shaped element 20 is made, for example, of $Al_2O_3$, and rests with its measured-gas-side end surface 21 against sealing ring 18.

A recess 30 which surrounds passthrough 24 is present in connector-side end surface 22 of ceramic shaped element 20. A seal 31, which holds sensing element 26 in gas-tight fashion in ceramic shaped element 20, is located in recess 30. Seal 31 has a powdered sealing packing 32 and a fusible glass seal 33. The fusible glass seal 33 is arranged above sealing packing 32.

Sealing packing 32 is made, for example, of steatite, graphite, boron nitride, or a mixture of these substances. To manufacture powdered sealing packing 32, a presintered and/or precompressed shaped member is, for example, manufactured from the aforesaid material and is placed into recess 30. By way of a compressive force acting on the shaped member, the shaped member is deformed into its powder constituents. During deformation, the powder comes into contact against sensing element 26 and against the wall of recess 30. Sensing element 26 is thereby pre-immobilized in passthrough 24, and at the same time a first seal is achieved. An alternative for manufacturing sealing packing 32 consists in placing into recess 30 a ceramic film made, for example, of $Al_2O_3$ or $ZrO_2$ in the green state, and sintering it at, for example, 80 degrees C while applying a compressive force. Application of the compressive force also causes a powder packing to be created during such sintering, so that the ceramic powder makes contact against the wall of recess 30 and against sensing element 26.

The fusible glass seal is made, for example, of a lithium aluminum silicate glass or lithium barium aluminum silicate glass. The fusible glass seal is manufactured, after sealing packing 32 in powder form has been manufactured, by introducing glass powder or glass particles into recess 30. In this state, the seal arrangement is heated to the melting temperature of the glass being used. The glass powder or glass particles thereby melt and join to the wall of recess 30 and to sensing element 26. This creates an absolutely gas-tight and gasoline-resistant seal 31 for sensing element 20 26 in the ceramic shaped element.

A gas-tight and gasoline-resistant seal between ceramic shaped element 20 and housing 12 is produced by way of sealing ring 18, in which ceramic shaped element 20 is pressed by way of a metal sleeve 36 onto sealing ring 18. Metal sleeve 36 has, for example distributed uniformly, multiple inwardly facing prongs 37 which engage into notches 38 shaped into housing 12. It is equally possible, however, to weld metal sleeve 36 to housing 12.

Measured-gas-side end section 27 of sensing element 26 projects out of housing 12 and is surrounded by a protective tube 40. The protective tube 40 has multiple gas inlet and gas outlet openings 41.

Connector contacts 43 are configured on sensing element 26 on connector-side end section 28; contact to connector contacts 43 is made with a connector plug (not depicted)

equipped with connector cables. Connector-side end section 28 projecting out of housing 12 is moreover surrounded by an encapsulation (not depicted) which surrounds the connector plug and protects end section 28 from environmental influences.

Application of the seal arrangement according to the present invention is not confined to the sealing of solid electrolyte sensing elements. It is also suitable for other temperature-stable and gas-tight seals between ceramic members.

What is claimed is:

1. A sensor for determining an oxygen content of an exhaust gas of an internal combustion engine, comprising:
    a metal housing including a longitudinal bore;
    a ceramic shaped holder element situated in the longitudinal bore of the metal housing;
    a hybrid seal including a fusible glass seal and at least one powdered sealing packing; and
    a sensing element situated in the ceramic shaped holder element in a gas-tight manner via the hybrid seal.

2. The sensor according to claim 1, wherein the at least one powdered sealing packing is arranged between the ceramic shaped element and the fusible glass seal.

3. The sensor according to claim 1, wherein the ceramic shaped element includes a recess in which the at least one powdered sealing packing and the fusible glass seal are arranged in direct contact with each other.

4. The sensor according to claim 3, wherein the recess is arranged on an end surface of the ceramic shaped element facing away from the exhaust gas.

5. The sensor according to claim 1, wherein the at least one powdered sealing packing is formed of a ceramic.

6. The sensor according to claim 4, wherein:
    the at least one powdered sealing packing is insertable as a shaped member into the recess, and
    the at least one powdered sealing packing is then deformed by transformation into a compact powder form by application of a compressive force.

7. The sensor according to claim 6, wherein at least one of a presintering operation and a precompressed operation is performed on the shaped member.

8. The sensor according to claim 7, wherein the shaped member is formed of one of steatite, graphite, boron nitride, $Al_2O_3$, $ZrO_2$, and a mixture of at least two of steatite, graphite, boron nitride, $Al_2O_3$, and $ZrO_2$.

9. The sensor according to claim 6, wherein:
    the shaped member is insertable into the recess as a green state type of ceramic film, and
    the shaped member is deformed by performing a hot-pressing operation on the green ceramic film.

10. The sensor according to claim 9, wherein the green ceramic film is formed of one of $Al_2O_3$, $ZrO_2$, or a mixture of $Al_2O_3$ and $ZrO_2$.

11. The sensor according to claim 1, wherein the fusible glass seal is formed of one of a lithium aluminum silicate glass and a lithium barium aluminum silicate glass.

12. The sensor according to claim 1, wherein the fusible glass seal and one powdered sealing packing contact the sensing element.

13. A method of manufacturing a sensor for determining an oxygen content of an exhaust gas of an internal combustion engine comprising:
    providing a metal housing including a longitudinal bore and a ceramic shaped holder situated in the longitudinal bore;
    providing a sensing element disposed in the ceramic shaped holder;
    packing a precompressed powder shaped member around a portion of the sensing element;
    compressing the presintered powder shaped member to form a first seal;
    introducing glass powder around a portion of the sensing element;
    heating the glass powder to form a second seal.

14. The method of claim 12, wherein the powder shaped member is presintered.

15. The method of claim 12, wherein the glass is particles.

16. A method of forming a sensor for determining an oxygen content of an exhaust gas of an internal combustion engine, comprising:
    forming a metal housing including a longitudinal bore;
    forming a ceramic shaped holder element situated in the longitudinal bore of the metal housing;
    forming a hybrid seal including a fusible glass seal and at least one powdered sealing packing; and
    forming a sensing element situated in the ceramic shaped holder element in a gas-tight manner via the hybrid seal.

* * * * *

UNITED STATES PATENT AND TRADEMARK OFFICE
CERTIFICATE OF CORRECTION

PATENT NO. : 6,223,583 B1
DATED : May 1, 2001
INVENTOR(S) : Friese et al.

It is certified that error appears in the above-identified patent and that said Letters Patent is hereby corrected as shown below:

Column 2,
Line 50, change "20 26" to -- 26 --
Line 50, change "shaped element." to -- shaped element 20. --

Signed and Sealed this

Twenty-sixth Day of August, 2003

JAMES E. ROGAN
*Director of the United States Patent and Trademark Office*